(12) United States Patent
Kim et al.

(10) Patent No.: US 10,677,806 B2
(45) Date of Patent: Jun. 9, 2020

(54) COMPOSITION FOR DIAGNOSING FOLLICULAR THYROID CARCINOMA USING EXPRESSION LEVEL OF AMINOACYL-TRNA SYNTHETASE-RELATED PROTEIN AND METHOD FOR DETECTING DIAGNOSTIC MARKER

(71) Applicants: MEDICINAL BIOCONVERGENCE RESEARCH CENTER, Gyeonggi-do (KR); THE ASAN FOUNDATION, Seoul (KR); UNIVERSITY OF ULSAN FOUNDATION FOR INDUSTRY COOPERATION, Ulsan (KR)

(72) Inventors: Sunghoon Kim, Seoul (KR); Won Suk Yang, Gyeonggi-do (KR); Kyunggon Kim, Seoul (KR); Won Gu Kim, Seoul (KR)

(73) Assignees: MEDICINAL BIOCONVERGENCE RESEARCH CENTER, Gyeonggi-do (KR); THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 0 days.

(21) Appl. No.: 16/233,695

(22) Filed: Dec. 27, 2018

(65) Prior Publication Data
US 2019/0277865 A1    Sep. 12, 2019

Related U.S. Application Data

(63) Continuation of application No. PCT/KR2017/007042, filed on Jul. 3, 2017.

(30) Foreign Application Priority Data

Jul. 1, 2016 (KR) .................. 10-2016-0083361

(51) Int. Cl.
| | | |
|---|---|---|
| G01N 33/53 | (2006.01) | |
| G01N 33/78 | (2006.01) | |
| G01N 33/573 | (2006.01) | |
| G01N 33/574 | (2006.01) | |

(52) U.S. Cl.
CPC .......... *G01N 33/78* (2013.01); *G01N 33/573* (2013.01); *G01N 33/574* (2013.01); *G01N 33/57407* (2013.01)

(58) Field of Classification Search
None
See application file for complete search history.

(56) References Cited

U.S. PATENT DOCUMENTS

2008/0015143 A1* 1/2008 Roman .............. C07K 14/4703
435/6.14

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Park et al., Aminoacyl tRNA synthetases and their connections to disease, PNAS, Aug. 12, 2008, vol. 105, No. 32, pp. 11043-11049. (Year: 2008).*
International Search Report corresponding to International Patent Application No. PCT/KR2017/007042 dated Sep. 20, 2017.
Kim et al., "Cancer Association Study of Aminoacyl-tRNA Synthetase Signaling Network in Glioblastoma," PloS One, vol. 7, Iss. 8. thesis No. e40960, pp. 1-11 (2012).
Lee et al., "Chemical Suppression of an Oncogenic Splicing Variant of AIMP2 Induces Tumour Regression," Biochemical Journal, vol. 454, pp. 411-416 (2013).
Nam et al., "Suppression of lysyl-tRNA synthetase, KRS, causes incomplete epithelial-mesenchymal transition and ineffective cell-extracellular matrix adhesion for migration," International Journal of Oncology, vol. 48, pp. 1553-1560 (2016).
Park et al., "Secreted human glycyl-tRNA synthetase implicated in defense against ERK-activated tumorigenesis," PNAS, vol. 109, pp. E640-E647 (2012).
Pfeifer et al., "Molecular differential diagnosis of follicular thyroid carcinoma and adenoma based on gene expression profiling by using formalin-fixed paraffin-embedded tissues," BMC Medical Genomics, vol. 6, No. 38, pp. 1-10 (2013).
Zhao et al., "Differentiation of Human Follicular Thyroid Adenomas from Carcinomas by Gene Expression Profiling," Oncology Reports, vol. 19, pp. 329-337 (2008)
IPRP and Written Opinion corresponding to International Patent Application No. PCT/KR2017/007042 dated Jan. 1, 2019.
Wiseman et al., "Molecular phenotyping of thyroid tumors identifies a marker panel for differentiated thyroid cancer diagnosis," Ann Surg Oncol., 15(10):2811-26 (2008).

\* cited by examiner

*Primary Examiner* — Gary Counts
(74) *Attorney, Agent, or Firm* — Jenkins, Wilson, Taylor & Hunt, P.A.

(57) ABSTRACT

A method for diagnosing follicular thyroid carcinoma is described. The method measures protein expression levels of an aminoacyl-tRNA synthetase (ARS) or an aminoacyl-tRNA synthetase complex-interacting multifunctional protein (AIMP) in a sample, such as a thyroid tissue sample, from a subject suspected of having follicular thyroid carcinoma. The protein expression levels of ARS or AIMP are compared to the measured protein expression levels in a control.

13 Claims, 6 Drawing Sheets
(6 of 6 Drawing Sheet(s) Filed in Color)

COMPOSITION FOR DIAGNOSING FOLLICULAR THYROID CARCINOMA USING EXPRESSION LEVEL OF AMINOACYL-TRNA SYNTHETASE-RELATED PROTEIN AND METHOD FOR DETECTING DIAGNOSTIC MARKER

CROSS REFERENCE TO RELATED APPLICATIONS

The presently disclosed subject matter is a continuation of and claims the benefit of PCT International Patent Application Serial No. PCT/KR2017/007042, filed Jul. 3, 2017, which claims the benefit of Korean Patent Application Serial No. 10-2016-0083361, filed Jul. 1, 2016, the disclosures of which are incorporated herein by reference in their entireties.

TECHNICAL FIELD

The present invention relates to a method for detecting markers for the diagnosis of follicular thyroid carcinoma using an expression level of aminoacyl-tRNA synthetase-related protein. More specifically, the present invention relates to a method for detecting markers of follicular carcinoma in order to provide information necessary for the diagnosis of follicular thyroid carcinoma in a patient suspected of having follicular thyroid carcinoma, the method comprising the steps of; a) obtaining a sample from a subject suspected of having follicular thyroid carcinoma; (b) measuring the protein expression level of an aminoacyl-tRNA synthetase (ARS) or an aminoacyl-tRNA synthetase complex-interacting multifunctional protein (AIMP) in the sample; and (c) comparing the measured protein expression level with that of a control, and determining that the subject having a change in the protein expression level has follicular thyroid carcinoma.

BACKGROUND OF THE INVENTION

The present application claims priority from Korean Patent Application No. 10-2016-0083361, filed on Jul. 1, 2016, the entire content of which is incorporated herein by reference.

Follicular thyroid carcinoma (FTC), which accounts for about 20% of all thyroid cancers, is frequently found in women and belongs to a differentiated thyroid cancer with good prognosis. Thyroid follicular carcinoma is mainly found in older ages, compared to papillary thyroid carcinoma which is the most common thyroid cancer. Papillary thyroid carcinoma is mainly metastasized through the lymph nodes, whereas thyroid follicular carcinoma through the blood vessels. On the other hand, papillary thyroid carcinoma can be diagnosed relatively easily through fine needle aspiration test by observing characteristic nuclear morphology. However, thyroid follicular carcinoma has difficulties in accurately diagnosing it because definite criteria have not been established. In particular, thyroid follicular carcinoma can be mistaken for follicular adenoma because 20-30% of follicular adenomas, which are benign tumors of the thyroid gland, cannot be distinguished from thyroid follicular carcinoma by fine needle aspiration test.

Currently, the confirmation of thyroid follicular carcinoma is possible only be collecting thyroid tissues through surgery and identifying the pathology in the tissues. In this way, pathologic examination including surgery is first performed by the surgical excision of the half of the thyroid where nodules is found, followed by histological examination. In case where thyroid follicular carcinoma is diagnosed, such a method is a very cumbersome method because the other half of the thyroid must be removed again through surgery, except for early cancer with good prognosis. Therefore, it is necessary to develop a biomarker that can distinguish thyroid follicular carcinoma from follicular adenoma and confirm thyroid follicular carcinoma, in the thyroid tissue or blood obtained during the fine needle aspiration test. In particular, when a protein-based biomarker is developed, the level of expression of the marker can be measured using an antibody or the like, so that information necessary for diagnosis can be quickly obtained, without a necessity to perform surgery for pathologic examination.

Mutations in genes such as BRAF, RET/PTC, RAS, PAX8/PPAR gamma, and P53, which have been proposed as biomarkers for thyroid follicular cancer, are not actually used in diagnosis because their incidence is not high. In addition, studies in which the expression levels of five genes such as ELMO1, EMCN, ITIH5, KCNAB1, and SLCO2A1 were reduced in thyroid follicular carcinoma tissues compared to follicular adenoma tissues, suggested a possibility of developing such genes as a marker that can distinguish follicular adenoma from thyroid follicular carcinoma. However, there is a limitation to utilize such genes as a marker; including the necessity of the process of extracting mRNAs from tissue (Pfeifer et al. *BMC Medical Genomics* 2013, 6:380). Protein markers that identify thyroid cancer are used as immunohistochemistry (Wiseman S M et al., *Annals of Surgical Oncology* 2008, 15:2811-2826), but their specificity is too low to distinguish thyroid follicular carcinoma from follicular adenoma.

Therefore, it is urgent to develop a biomarker that can specifically distinguish thyroid follicular carcinoma from benign tumors such as follicular adenoma.

DETAILED DESCRIPTION OF THE INVENTION

Technical Problem

Accordingly, the present inventors collect pathologic tissues from patients diagnosed with thyroid follicular carcinoma and follicular adenoma, respectively, and analyzed the level of a various proteins by mass spectrometry. As a result, it was confirmed that the level of various aminoacyl-tRNA synthetase-related proteins are distinguishable between thyroid follicular carcinoma and follicular adenoma tissue, thus completing the present invention.

Accordingly, an aspect of the present invention is to provide a method for providing information necessary for diagnosis of follicular thyroid carcinoma, the method comprising the steps of:

(a) obtaining a sample from a subject suspected of having follicular thyroid carcinoma;

(b) measuring the protein expression level of an aminoacyl-tRNA synthetase (ARS) or an aminoacyl-tRNA synthetase complex-interacting multifunctional protein (AIMP) in the sample; and (c) comparing the measured protein expression level with that of a control, and determining that the subject having a change in the protein expression level has follicular thyroid carcinoma.

Technical Solution

An embodiment according to an aspect of the present invention provides a method for providing information necessary for diagnosis of follicular thyroid carcinoma, the method comprising the steps of:

(a) obtaining a sample from a subject suspected of having follicular thyroid carcinoma;

(b) measuring the protein expression level of an aminoacyl-tRNA synthetase (ARS) or an aminoacyl-tRNA synthetase complex-interacting multifunctional protein (AIMP) in the sample; and (c) comparing the measured protein expression level with that of a control, and determining that the subject having a change in the protein expression level has follicular thyroid carcinoma Hereinafter, the present invention will be described in detail.

The present invention provides a method for providing information necessary for diagnosis of follicular thyroid carcinoma, the method comprising the steps of:

(a) obtaining a sample from a subject suspected of having follicular thyroid carcinoma;

(b) measuring the protein expression level of an aminoacyl-tRNA synthetase (ARS) or an aminoacyl-tRNA synthetase complex-interacting multifunctional protein (AIMP) in the sample; and (c) comparing the measured protein expression level with that of a control, and determining that the subject having a change in the protein expression level has follicular thyroid carcinoma.

The step (a) is a step of obtaining a sample from a subject in order to provide information necessary for diagnosis of follicular thyroid carcinoma in the subject suspected of having follicular thyroid carcinoma, according to the method of the present invention.

As used herein, the term 'diagnosis' or 'diagnosing' means identifying the presence or characteristic of a certain pathological condition. Herein, the 'diagnosis' or 'diagnosing' refers to the measurement of the expression level of aminoacyl tRNA (ARS) or aminoacyl tRNA synthetase complex-interacting multifunctional protein (AIMP) to determine the occurrence of thyroid follicular carcinoma, in particular differentially identifying thyroid follicular carcinoma from benign tumors, such as follicular adenoma.

As used herein, the term 'follicular thyroid carcinoma (FTC)' is a malignant tumor of the thyroid gland. It is one of the differentiated thyroid cancers that develops mainly in the glandular tissue associated with the production of thyroid hormone. It is characterized by its metastasis to other tissues through the blood stream. Thyroid follicular carcinoma is often diagnosed as a thyroid nodule incidentally without pain by ultrasound examination, palpation, and the like during a medical examination. Thyroid cancer is diagnosed by examining the size, location, and shape of the thyroid tumor through thyroid ultrasonography. Thyroid gland is pierced with a fine needle while observing the thyroid by ultrasonography, thyroid cells are collected and their cell shapes are checked (fine needle aspiration cytology). However, the cell shape of thyroid follicular carcinoma, is not distinguishable from that of benign tumors such as follicular adenoma (FA). Therefore, the current diagnostic method is to collect pathological tissues by a surgical method and confirm it by biopsy. It is not efficient, even if it is not clear whether it is a malignant tumor, and since reoperation is required to completely remove the tumor if it is confirmed to be a malignant tumor.

Accordingly, the present invention provides a novel diagnostic marker and method that can clearly diagnose thyroid follicular carcinoma by a non-surgical method in a patient with a tumor or nodule found in his or her thyroid that needs to be checked for its malignancy.

In one embodiment, the present inventors identified more than 4000 proteins by mass spectrometry (MS) and protein sequencing in thyroid follicular carcinoma and follicular adenoma tissues and compared the protein levels in both pathological tissues. Gene ontology analysis showed that proteins related to oxidation/reduction, protein localization, and intracellular transport were prominent in follicular adenoma, whereas proteins related to proteolysis, macromolecule catabolic process, RNA processing, and cell cycle were predominated in thyroid follicular cancer.

In particular, among the identified proteins, after quantitative analysis of aminoacyl tRNA synthetase and its related proteins using MS peak area, it was confirmed that a large number of proteins have different expression levels in thyroid follicular carcinoma and follicular adenoma, respectively. Specifically, it was found that AARS, DARS, EPRS, WARS, GARS, IARS cytoplasmic, YARS, NARS, QARS, RARS, SARS cytoplasmic, and TARS showed decreased protein levels in thyroid follicular carcinoma, in comparison with follicular adenoma. On the other hand, AIMP1, IRS mitochondrial, SARS mitochondrial, KARS, VARS, and FARSA were found to have increased protein levels in thyroid follicular carcinoma.

Therefore, by using such differences in the levels of the aminoacyl-tRNA synthetase and related proteins identified by the present inventors, that is, by selecting one or more of the proteins described above and measuring the protein level in the sample of the subject, it can be understood that a diagnostic marker, capable of differentiating between follicular adenoma and follicular thyroid carcinoma which is difficult to cytologically distinguish, can be developed.

As described above, the subject in the method of the present invention may be a patient suspected of having follicular thyroid carcinoma. That is, the subject may be a patient who is found to have a tumor or nodule in his or her thyroid gland which needs to be differentiated between malignant follicular thyroid carcinoma and benign follicular adenoma In addition, the sample for the method of the present invention may be selected from the group consisting of thyroid tissue, blood, plasma, serum, lymph, and urine. The sample can be appropriately collected from the subject according to a known method and may be subjected to necessary pre-treatment according to protein detection methods.

The step (b) is a step of measuring the protein expression level of the aminoacyl-tRNA synthetase (ARS) or aminoacyl-tRNA synthetase complex-interacting multifunctional protein (AIMP) in the sample collected (separated) from the subject in the step (a).

As used herein, the term 'protein' is used interchangeably with 'polypeptide' or 'peptide', and refers to a polymer of amino acid residues such as ones commonly found in natural state proteins.

In the present invention, an 'aminoacyl-tRNA synthetase or an aminoacyl-tRNA ligase (ARS)' is an enzyme that mediates an aminoacylation reaction linking an amino acid to an appropriate tRNA. It is also called a tRNA ligase. Among the 20 amino acids, glutamic acid and proline are linked to tRNA in the cytoplasm by a single ARS, which is called bifunctional aminoayl-tRNA synthetase or bifunctional glutamyl-prolyl-tRNA synthetase. ARS is generally classified into Class I series that mediate aminoacylation reaction at the 2'-OH end of adenosine nucleotide of tRNA and Class II series that mediates aminoacylation reaction at 3'-OH end of adenosine nucleotide of tRNA. Class I series include arginine tRNA synthetase, cysteine tRNA synthetase, glutamic acid tRNA synthetase, glutamine tRNA synthetase, isoleucine tRNA synthetase, leucine tRNA synthetase, methionine tRNA synthetase, tryptophan tRNA synthetase, valine tRNA synthetase, and tyrosine tRNA synthetase. Class II series include alanine tRNA synthetase, aspartic acid tRNA synthetase, asparagine tRNA synthetase, glycine tRNA synthetase, histidine tRNA synthetase, lysine tRNA synthetase, phenyalanine tRNA synthetase, proline tRNA synthetase, threonine tRNA synthetase, and serine tRNA synthetase.

It present as a cytoplasmic or mitochondrial one depending on the location of its intracellular distribution, while being referred to as are existing in the cytoplasm unless otherwise indicated in the present specification.

As a biomarker for diagnosing follicular thyroid carcinoma from the viewpoint of the present invention, more specifically, ARS may be one or more proteins selected from isoleucyl-tRNA synthetase mitochondrial (IARS mitochondrial), seryl-tRNA synthetase mitochondrial (SARS mitochondrial), lysyl-tRNA synthetase (KARS), valyl-tRNA synthetase (VARS), phenylalanyl-tRNA synthetase (FARS) alpha subunit (FARSA), alanyl-tRNA synthetase (AARS), aspartyl-tRNA synthetase (DARS), bifunctional aminoacyl-tRNA synthetase or glutamyl-prolyl-tRNA synthetase (EPRS), tryptophanyl-tRNA synthetase (WARS), glycyl-tRNA synthetase (GARS), isoleucyl-tRNA synthetase cytoplasmic (IARS cytoplasmic), tyrosyl-tRNA synthetase (YARS), asparagyl-tRNA synthetase (NARS), glutaminyl-tRNA synthetase (QARS), arginyl-tRNA synthetase (RARS), seryl-tRNA synthetase cytoplasmic (SARS cytoplasmic) and threonyl-tRNA synthetase (TARS). If the ARSs are of human origin, the specific sequence thereof is not particularly limited, but the sequence information described in Table 5 of the present specification can be referred to.

As used herein, the 'aminoacyl-tRNA synthetase complex-interacting multifunctional protein (AIMP)' is a protein known to enhance the catalytic activity of the multi-tRNA synthetase complex (MSC) by binding to the multi-tRNA synthetase complex. In humans, aminoacyl-tRNA synthetase complex-interacting multifunctional protein 1 (AIMP1), aminoacyl-tRNA synthetase complex-interacting multifunctional protein 2. (AIMP2), aminoacyl-tRNA synthetase complex-interacting multifunctional protein 3 (AIMP3) and the like have been reported. More specifically, the AIMP in the present invention may be AIMP1, also known as p43. If the AIMP (particularly AIMP1) are of human origin, the specific sequence thereof is not particularly limited, but the sequence information described in Table 5 of the present specification can be referred to.

As used herein, the term 'expression' means that a protein or a nucleic acid is produced in a cell. In the present invention, a method of measuring protein expression level can be performed by appropriately selecting known methods. For example, such method include western blotting, dot blotting, enzyme-linked immunosorbent assay (ELISA), radio immunoassay (RIA), radial immunodiffusion assay, Ouchterlony immunodiffusion assay, rocket immunoelectrophoresis, immunohistochemistry, immunoprecipitation, complement fixation assay, Flow cytometry (FACS), protein chips and mass spectrometry, but are not limited thereto. Most preferably, the protein level in the sample can be measured by mass spectrometry.

The step (c) is a step of comparing the measured protein expression level with that of a control, and determining that the subject having a change in the protein expression level has follicular thyroid carcinoma.

When the level of expression of ARS or AIMP measured in a subject suspected of having follicular thyroid carcinoma is compared with that of the control group, In case, the level of one or more proteins selected from aminoacyl-tRNA synthetase complex-interacting multifunctional protein 1(AIMP1), isoleucyl-tRNA synthetase mitochondrial (IARS mitochondrial), seryl-tRNA synthetase mitochondrial (SARS mitochondria), lysyl-tRNA synthetase (KARS), tyrosyl-tRNA synthetase (VARS) and phenylalanyl-tRNA synthetase alpha subunit (FARSA) is increased; and/or In case, the level of one or more proteins selected from alanyl-tRNA synthetase (AARS), aspartyl-tRNA synthetase (CARS), bifunctional aminoacyl-tRNA synthetase or glutamyl-prolyl-tRNA synthetase (EPRS), tryptophanyl-tRNA synthetase (WARS), glycyl-tRNA synthetase (GARS), isoleucyl-tRNA synthetase cytoplasmic (IARS cytoplasmic), tyrosyl-tRNA synthetase (MRS), asparagyl-tRNA synthetase (NARS), glutaminyl-tRNA synthetase (QARS), arginyl-tRNA synthetase (RARS), seryl-tRNA synthetase cytoplasmic (SARS cytoplasmic) and threonyl-tRNA synthetase (TARS) is decreased;

it can be determined that the subject has follicular thyroid carconoma, or that the thyroid tumor or nodule found in the subject is follicular thyroid carcinoma.

The control group is preferably a patient having a tumor or nodule on the thyroid gland which has been identified as a follicular adenoma (FA), a benign tumor. In this case, the level of the ARS or aminoacyl tRNA synthetase complex-binding multifunctional protein (AIMP) is measured beforehand in a plurality of FA patients prior to the detection of the follicular thyroid carcinoma marker in the subject, a range of a protein levels or baseline values expected from patients identified as FA is thereby obtained. Thereafter, the method of the present invention is performed in such a manner as to determine a difference in comparison with the protein level measured in a subject suspected of having follicular thyroid carcinoma.

The step of comparing the ARS or AIMP expression level of a subject suspected of having follicular thyroid carcinoma with the control group may be performed by any method without limitation as long as it can clearly differentiate FTC from FA using the marker protein according to the present invention. For example, as described in one embodiment herein, a value representing the ARS protein or AIMP protein expression level measured in the comparison group, that is, the concentration of the marker protein measured in the tissue sample or a value such as ion peak area of marker protein derived from MS analysis can be directly compared. In addition, the relative level between the comparison group, such as 'the ratio of ARS or AIMP protein expression levels in FTC patients versus FA patients', may be used as a criteria of such determination.

Furthermore, since the ARS or AIMP marker proteins listed above exhibit specific expression patterns that distinguish FA from FTC, in order to diagnose follicular thyroid carcinoma, multiple marker proteins may be selected to measure the expression level, and their expression pattern may be used to diagnose FTC based on their expression patterns. The expression pattern is a qualitative feature of expression which represents an indicator of the expression pattern, the expression ranking and the like of the marker proteins, observed by measuring and comparing the expression levels of a plurality of marker proteins.

The present invention also provides a composition for diagnosing thyroid follicular carcinoma, the composition comprising an agent for measuring the expression level of an aminoacyl-tRNA synthetase (ARS) or an aminoacyl-tRNA synthetase complex-interacting multifunctional protein (AIMP).

The present invention also provides use of an agent for measuring the expression level of an aminoacyl-tRNA synthetase (ARS) or an aminoacyl-tRNA synthetase complex-interacting multifunctional protein (AIMP) for the preparation of an agent for diagnosing thyroid follicular carcinoma.

The composition for diagnosing follicular thyroid carcinoma of the present invention may be a composition for distinguishing follicular adenoma from follicular thyroid carcinoma, and the specific types of ARS and AIMP, and their detection characteristics can be understood with reference to the above description.

The agent for measuring the ARS and AIMP expression level of the present invention is not particularly limited as long as it is a ligand that specifically adheres to the above-mentioned specific protein. For example, it may be a peptide, an antibody, or an aptamer having a binding domain specific for the above-mentioned protein, but is not limited thereto.

As used herein, the term 'antibody' means a specific immunoglobulin directed against an antigenic site, as used in the art. Any of those prepared through the above-mentioned one or more protein injections or commercially available can be used. In addition, the antibody includes a polyclonal antibody, a monoclonal antibody, a chimeric antibody, and a fragment capable of binding to an epitope.

As used herein, the term 'peptide' refers to a polypeptide that does not have the structure of the intact antibody, but has a specific antigen binding site (binding domain) directed against the antigenic site. The peptide comprises a functional fragment of an antibody molecule that is not a complete form of an antibody having two light chains and two heavy chains. The length of the peptide is not particularly limited, but may be, for example, 2 to 100 amino acids, preferably 5 to 50 amino acids.

As used herein, the term 'aptamer' refers to an oligonucleotide molecule having a binding activity to a specific target molecule. The aptamer may be RNA, DNA, modified nucleic acid or a mixture thereof, and may be in a linear or cyclic form.

The present invention also provides a kit for diagnosing a thyroid follicular carcinoma, the kit comprising an agent for measuring the expression level of an aminoacyl-tRNA synthetase (ARS) or an aminoacyl-tRNA synthetase complex-interacting multifunctional protein (AIMP).

The diagnostic kit of the present invention may comprise one or more other compositions (Reagents capable of detecting antibodies, such as labeled secondary antibodies, chromophores, enzymes (in conjugated form with antibodies) and other substance capable of binding to their substrates or antibodies, a washing solution or an eluent which can remove a substrate to be color-developed with an enzyme and unbound proteins and retain only a bound protein marker), solutions or devices suitable for an assay, as well as peptides, antibodies, and aptamers that selectively recognize the above-mentioned proteins as markers for measuring ARS or AIMP expression levels.

The present invention also provides a method for diagnosing thyroid follicular carcinoma, wherein the expression level of an aminoacyl-tRNA synthetase (ARS) or an aminoacyl-tRNA synthetase complex-interacting multifunctional protein (AIMP) in a sample of a subject is measured. The method for diagnosing follicular thyroid carcinoma may further comprise comparing ARS or AIMP expression level with that of the follicular adenoma patient, and determining the follicular thyroid carcinoma in the subject whose expression level has changed. The specific types and expression patterns of ARS or AIMP are as described above.

As used herein, the term 'subject' refers to an animal, preferably a mammal, particularly an animal including a human, more preferably a human or a patient who needs diagnosis. The subject is as described above.

The term "comprising" is used synonymously with "containing" or "being characterized", and does not exclude additional ingredients or steps that are not mentioned in the compositions and the methods. The term "consisting of" excludes additional elements, steps, or ingredients that are not specificity described. The term "consisting essentially of" means that in the scope of the compositions or methods, the term includes any material or step that does not substantially affect basic characteristics of the compositions or methods, as well as described materials or steps.

Advantageous Effect

Accordingly, the present invention provides a method for detecting a follicular thyroid carcinoma diagnosing marker using the expression level aminoacyl-tRNA synthetase related protein. The present inventors confirmed that the levels of a plurality of aminoacyl-tRNA synthetase and related proteins are different in follicular thyroid carcinoma tissues and follicular adenoma, which are benign tumors of the thyroid gland. Specifically, the types of proteins disclosed herein are capable of diagnosing follicular thyroid carcinoma easily and clearly without any tissue collection through surgery, and have high diagnostic sensitivity and specificity.

BRIEF DESCRIPTION OF DRAWINGS/FIGURES

The patent or application file contains at least one drawing executed in color. Copies of this patent or patent application publication with color drawing(s) will be provided by the Office upon request and payment of the necessary fee.

FIG. 1 shows the number of proteins identified as a result of proteomic analysis of follicular adenoma (FA) and follicular thyroid carcinoma (FTC) tissues.

FIG. 2 shows mass spectrometer (MS) results comparing the protein level of AIMP1, IARS mitochondrial, SARS mitochondrial, KARS, VARS, and FARSA (FARS alpha subunit) in follicular adenoma (FA) and follicular thyroid carcinoma (FTC) tissues, respectively. The y-axis of the graph represents an ion peak area detected by the mass spectrometer for peptides constituting the proteins, which can be used as a quantitative value.

MODE FOR CARRYING OUT INVENTION

Figure 1:
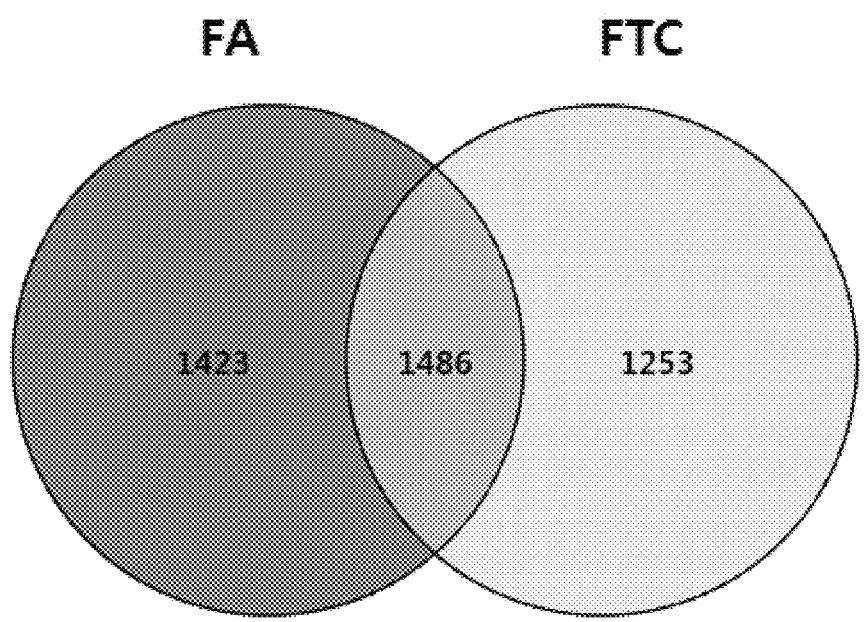

Hereinafter, the present invention will be described in detail.

However, the following examples are only illustrative of the present invention, and the present invention is not limited to the following examples.

Method

1. Clinical Sample

Thyroid tissue samples were used which were donated to Bio-Resource Center of the Asan Medical Center upon consent to donation of human tissue for a study. The study protocol was approved by the Asan Medical Center Institutional Review Board (approval number: 2013-0539). In this study, 10 cases of thyroid tissue collected from follicular thyroid carcinoma (FTC) patients and 10 cases of thyroid tissue collected from follicular adenoma (FA) patients were used as tissue samples. Patients were randomly selected regardless of their age and gender to minimize artificial bias.

2. Protein Analysis

Tissue homogenization was performed on the thyroid tissue collected from FTC and FA patients, respectively, and protein extraction was the performed with RIPA buffer supplemented with 1% SUS and protease/phosphatase inhibitor cocktail. The extracted proteins were quantitated with BCA, and 100 μg of each sample was mixed to prepare a pooling set. Peptides were prepared by the filter-aided sample preparation (FASP) method, followed by Nano LC-Q Exactive mass spectrometry and protein analysis. Specific experimental methods are as follows:

Fractionated on a 20 cm C18 capillary column (OD 360 μm, ID 75 μm) for 120 minutes;

Fractionated on gradient (5-45% acetonitrile and 0.1% formic acid solution) for 80 minutes;

Collecting data in data dependent acquisition (DDA) mode for Top 5 intensity precursor; and The collected data were compared with the sequence database using the Proteome discoverer 1.4 program and the peak area was analyzed. DAVID gene ontology analysis was also performed.

3. Western Blot Analysis 20 ug of thyroid tissue lysate collected from 10 FTC and 10 FA patients, respectively, were subjected to SDS PAGE electrophoresis. After the electrophoresed PAGE gel was transferred to polyvinylidene difluoride (PVDF) membrane (Millipore), and blocking with Bovine serum albumin was performed. The first reaction was a monoclonal mouse anti-human AIMP1 antibody (1:500) and mouse anti-human beta actin (1:1000) antibody reacted for 6 hours at 4° C., followed by blot detection using goat anti-mouse HRP-conjugated secondary antibody (1:4000). Band Intensity was measured using ImageJ (version 1.48), while Receiver Operating Characteristics (ROC) analysis, Area Under Curve (AUC), and intact plot analysis were performed using Med-Calc (version 17.6).

Example 1

Identification of Thyroid Tissue Proteins

A total of 2,909 proteins in follicular adenoma tissues and 2,739 proteins in follicular thyroid carcinoma tissues were identified, respectively, while a total of 4,162 proteins were identified (FIG. 1). This is the most extensive thyroid cancer-related protein analysis results that has not been reported in the art so for.

Example 2

Gene Ontology Analysis

As a result of Gene ontology analysis, the functional classification of proteins related to oxidation/reduction, protein localization, and intracellular transport was prominent in follicular adenoma groups (Table 2), whereas the functional classification of proteolysis, macromolecule catabolic process, RNA processing and cell cycle related proteins was differentiated in follicular thyroid carcinoma groups (Table 1).

TABLE 1

Proteins that are specifically expressed in FTC
Functional annotation (FTC Specific proteome)

| Term | RT | Count | % | P-value | Benjamin |
|---|---|---|---|---|---|
| Proteolysis | RT | 65 | 8.9 | 4.9E−3 | 1.9E−1 |
| protein localization | RT | 59 | 8.0 | 1.3E−3 | 6.4E−2 |
| establishment of protein localization | RT | 56 | 7.6 | 2.3E−4 | 1.6E−2 |
| intracellular transport | RT | 55 | 75 | 6.2E−6 | 6.2E−4 |
| protein transport | RT | 54 | 7.4 | 5.8E−4 | 3.4E−2 |
| macromolecule catabolic process | RT | 54 | 7.4 | 1.0E−3 | 5.3E−2 |
| RNA processing | RT | 50 | 6.8 | 1.6E−6 | 2.1E−4 |
| cell cycle | RT | 50 | 6.8 | 6.4E−3 | 2.1E−1 |
| negative regulation of macromolecule metabolic process | RT | 49 | 6.7 | 3.6E−3 | 1.5E−1 |
| positive regulation of macromolecule metabolic process | RT | 49 | 6.7 | 4.9E−2 | 5.9E−1 |

TABLE 2

Proteins that are specifically expressed in FA
Functional annotation (FA specific proteome)

| Term | RT | Count | % | P-value | Benjamin |
|---|---|---|---|---|---|
| oxidation reduction | RT | 56 | 7.1 | 4.0E−6 | 5.3E−3 |
| protein localization | RT | 54 | 6.8 | 2.3E−2 | 6.2E−1 |
| intracellular transport | RT | 52 | 6.6 | 1.4E−4 | 3.9E−2 |
| protein transport | RT | 50 | 6.3 | 9.1E−3 | 4.5E−1 |
| establishment of protein localization | RT | 50 | 6.3 | 1.1E−2 | 4.7E−1 |
| phosphorylation | RT | 48 | 6.1 | 4.3E−2 | 7.0E−1 |
| translation | RT | 45 | 5.7 | 1.5E−10 | 3.9E−7 |
| biological adhesion | RT | 45 | 5.7 | 1.9E−2 | 5.9E−1 |
| cell adhesion | RT | 45 | 5.7 | 2.0E−2 | 5.9E−1 |
| vesicle-mediated transport | RT | 44 | 5.5 | 1.0E−3 | 1.5E−1 |

In particular, among the proteins specifically expressed in follicular thyroid carcinoma thyroid tissue, the focal adhesion-related proteins were significantly increased compared to follicular adenoma thyroid tissue. Also, spliceosome-related proteins were found to be specifically increased in follicular thyroid carcinoma.

Example 3

Trend Analysis of ARS (Aminoacyl-tRNA Synthetase)-Related Protein Expression

Among the proteins identified from the analysis result, ARS-related proteins were selected and label free semi-quantification was performed based on the peak area. As a result, 20 ARS and AIMP in follicular adenoma, 21 ARS and AIMP in follicular thyroid carcinoma tissues were identified, and quantitative analysis results are shown in the table below (Table 3, Table 4).

TABLE 3

ARS and AIMP proteins expressed in FA
ARSs in Follicular adenoma tissue

| Description | Gene symbol | Uniprot ID | Peak Area |
|---|---|---|---|
| Alanine-tRNA ligase, cytoplasmic | AARS | SYAC_HUMAN | 1125849500 |
| Aminoacyl tRNA synthase complex-interacting multifunctional protein 1 | AIMP1 | AIMP1_HUMAN | 85053716 |
| Aminoacyl tRNA synthase complex-interacting multifunctional protein 2 | AIMP2 | A8MU58_HUMAN | 71773240 |
| Arginine-tRNA ligase, cytoplasmic | RARS | SYRC_HUMAN | 661244666 |
| Asparagine-tRNA ligase, cytoplasmic | NARS | SYNC_HUMAN | 943432533 |
| Aspartyl-tRNA synthetase, isoform CRA | DARS | D3DP78_HUMAN | 796052746 |
| Bifunctional glutamate/proline-tRNA ligase | EPRS | SYEP_HUMAN | 1905052478 |
| Glycine-tRNA liagase | GARS | SYG_HUMAN | 289437841 |
| Isoleucine-tRNA ligase. Cytoplasmic | IARS | J3KR24_HUMAN | 5433348221 |
| Isoleucine-tRNA ligase, mitochondrial | IARS2 | SYMI_HUMAN | 310599507 |
| Lysine-tRNA ligase | KARS | SYK_HUMAN | 171681552 |
| Phenylalanine-tRNA ligase alpha subunit | FARSA | B4E363_HUMAN | 91568703 |
| QARS protein (Fragment) | QARS | Q96AW5_HUMAN | 382807833 |
| Serine-tRNA ligase, cytoplasmic | SARS | SYSC_HUMAN | 13939590732 |
| Serine-tRNA ligase, mitochondrial | SARS2 | SYSM_HUMAN | 54572943 |
| Threonine-tRNA ligase, cytoplasmic | TARS | SYTC_HUMAN | 366450168 |
| Tryptophan-tRNA ligase, cytoplasmic | WARS | SYWC_HUMAN | 1005292231 |
| Tyrosine-tRNA ligase, cytoplasmic | YARS | SYYC_HUMAN | 2381826769 |
| Tyrosine-tRNA ligase, mitochondrial | YARS2 | SYYM_HUMAN | 78858264 |
| Valyl-tRNA synthetase (Fragment) | VARS | A2BEY0_HUMAN | 112446540 |

TABLE 4

ARS and AIMP proteins expressed in FTC
ARSs in Follicular thyroid carcinam tissue

| Description | Gene symbol | Uniprot ID | Peak Area |
|---|---|---|---|
| Aspartate-tRNA ligase, cytoplasmic | DARS | SYDC_HUMAN | 676501313 |
| Isoleucine-tRNA, mitochondrial | IARS2 | SYIM_HUMAN | 405032150 |
| Serine-tRNA ligase, cytoplasmic | SARS | Q5T5C7_HUMAN | 6841913593 |
| Alanine-tRNA ligase, cytoplasmic | AARS | SYAC_HUMAN | 259092335 |
| Asparagine-tRNA ligase, cytoplasmic | NARS | SYNC_HUMAN | 699339102 |
| Tryptophan-tRNA ligase, cytoplasmic | WARS | SYWC_HUMAN | 488259749 |
| Tyrosine-tRNA ligase, cytoplasmic | YARS | SYYC_HUMAN | 28939829 |
| Valine-tRNA ligase | VARS | B0V043_HUMAN | 380930687 |
| Phenylalanine-tRNA ligase alpha subunit | FARSA | SYFA_HUMAN | 116709397 |
| Histidine-tRNA ligase, cytoplasmic | HARS | J3KNE5_HUMAN | 244441275 |
| Threonine-tRNA ligase, cytoplasmic | TARS | B5DEG8_HUMAN | 226134539 |
| FARSB protein (Fragment) | FARSB | Q9BR63_HUMAN | 209463210 |
| Cysteine-tRNA ligase, cytoplasmic | CARS | B4DKY_HUMAN | 64458226 |
| Glutamine-tRNA ligase | QARS | SYQ_HUMAN | 293130531 |
| Serine--tRNA ligase, mitochondrial | SARS2 | SYSM_HUMAN | 3864844815 |
| Glycine-tRNA ligase | GARS | SYG_HUMAN | 276263425 |
| Isoleucine-tRNA ligase, cytoplasmic | IARS | J3KR24_HUMAN | 229288160 |

TABLE 4-continued

ARS and AIMP proteins expressed in FTC
ARSs in Follicular thyroid carcinam tissue

| Description | Gene symbol | Uniprot ID | Peak Area |
|---|---|---|---|
| Aminoacyl tRNA synthase complex-interacting multifunctional protein 1 | AIMP1 | AIMP1_HUMAN | 412726062 |
| Lysine-tRNA ligase | KARS | SYK_HUMAN | 127812747 |
| Bifunctional glutamate/proline-tRNA ligase | EPRS | SYEP_HUMAN | 399164615 |
| Arginine-tRNA ligase, cytoplasmic | RARS | SYRC_HUMAN | 196971392 |

Figure 2:
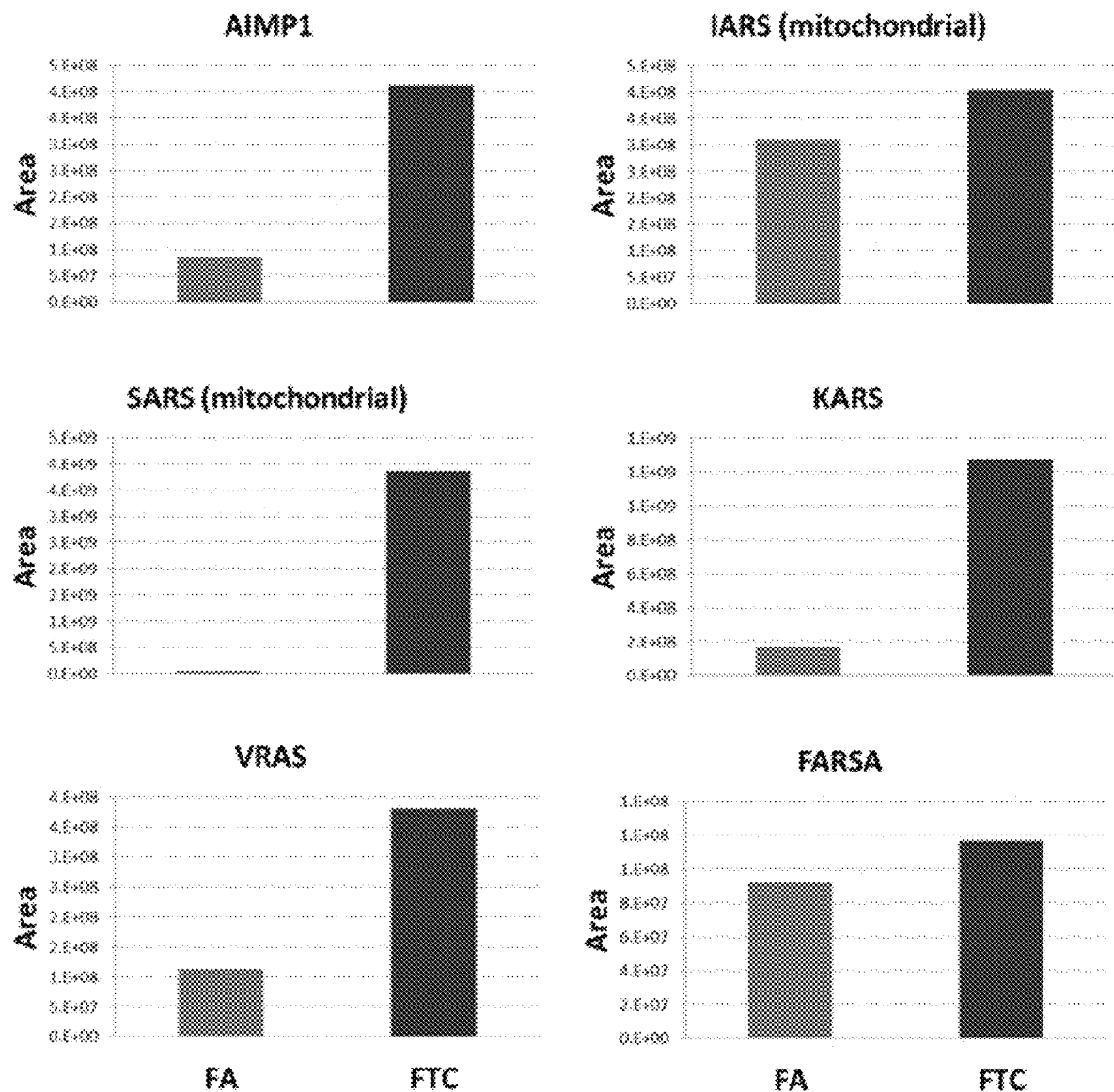
Figure 3:
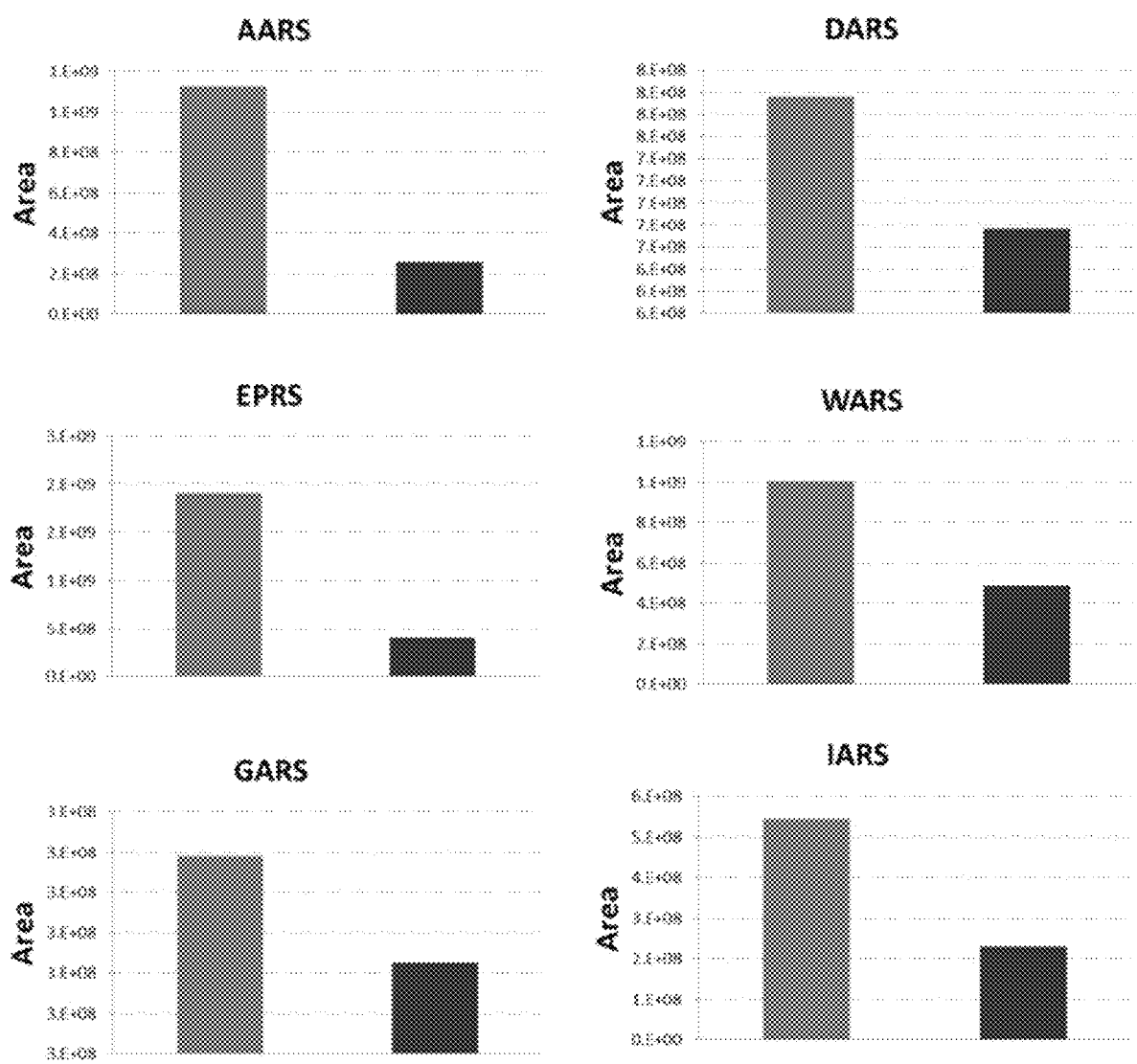
FIG. 3 shows mass spectrometer (MS) results comparing the protein level of AARS, DARS, EPRS, WARS, GARS, and IASRS cytoplasmic in follicular adenoma (FA) and follicular thyroid carcinoma (FTC) tissues, respectively. The y-axis of the graph represents an ion peak area detected by the mass spectrometer for peptides constituting the proteins, which can be used as a quantitative value.

In particular, AARS is decreased and AIMP1, KARS and VARS are increased in follicular thyroid carcinoma tissue, compared with follicular adenoma tissue (FIG. 2 and FIG. 3). The increase of AIMP1 and KARS in follicular thyroid carcinoma tissues compared to benign tumors of follicular adenomas was confirmed for the first time in this study.

Figure 4:
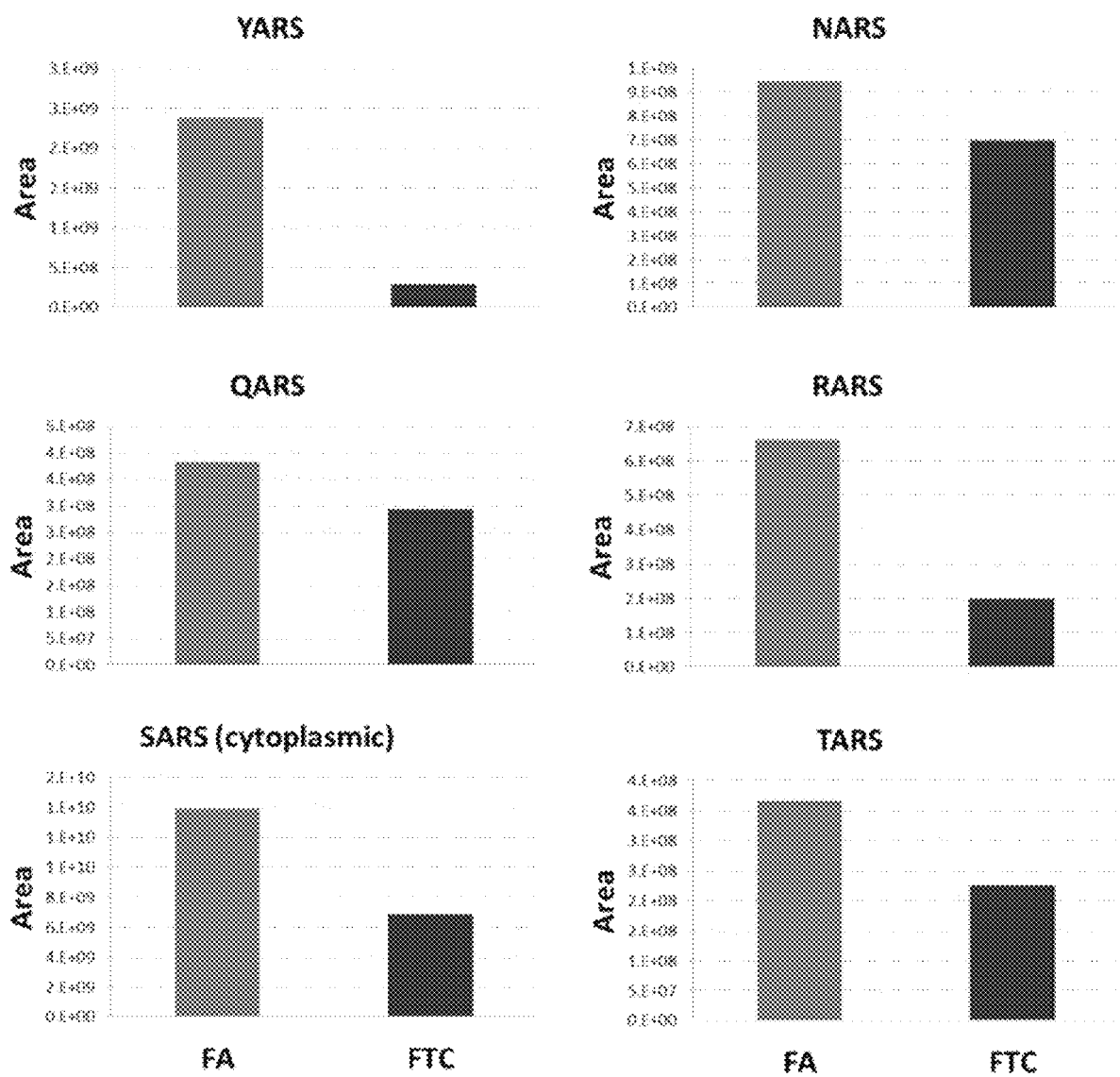
FIG. 4 shows mass spectrometer (MS) results comparing the protein level of YARS, NARS, QARS, RARS, SARS cytoplasmic, and TARS in follicular adenoma (FA) and follicular thyroid carcinoma (FTC) tissues, respectively. The y-axis of the graph represents an ion peak area detected by the mass spectrometer for peptides constituting the proteins, which can be used as a quantitative value.

In addition to, AARS, aspartate-tRNA ligase (DARS), bifunctional glutamate/proline-tRNA ligase (EPRS), tryptophan-tRNA ligase (WARS), glycine-tRNA ligase (GARS), isoleucine-tRNA ligase cytoplasmic (EARS cytoplasmic), tyrosine-tRNA ligase (PARS), asparagine-tRNA ligase (MARS), glutamine-tRNA ligase (QARS), arginine-tRNA ligase (RARS), serine-tRNA ligase cytoplasmic (SARS cytoplasmic), threonine-tRNA ligase (TARS) and the like showed decreased protein levels in follicular thyroid carcinomas compared to follicular adenomas (FIG. 3 and FIG. 4). In contrast, AIMP1, isoleucine-tRNA ligase mitochondrial (IARS mitochondrial), serine-tRNA ligase mitochondrial (SARS mitochondrial), lysine-tRNA ligase (KARS), valine-tRNA ligase (VARS), phenylalanine-tRNA ligase alpha subunit (FARS alpha subunit) and the like showed the opposite tendency (FIG. 2). The proteins showing this difference can be used as biomarkers to differentiate follicular thyroid carcinoma from follicular adenomas, and sequence information of the biomarkers discovered in the present invention is provided in Table 5 below.

TABLE 5

| Classification | Gene symbol | seq. reference (GenBank GI No.) |
|---|---|---|
| up | AIMP1 | 215490009 |
| | IARS mitochondrial | 94730583 |
| | SARS mitochondria | 23822219 |
| | KARS | 20178333 |
| | VARS | 1194845281 |
| | FARSA | 12643946 |
| down | AARS | 115502460 |
| | DARS | 20178330 |
| | EPRS | 288558855 |
| | WARS | 135191 |
| | GARS | 313104283 |
| | IARS cytoplasmic | 239938717 |
| | YARS | 13638438 |
| | NARS | 3915059 |
| | QARS | 1351170 |
| | RARS | 20178331 |
| | SARS cytoplasmic | 19860217 |
| | TARS | 60267755 |

Example 4

Quantitative Analysis of AIMP1 Protein in FA and FTC Groups

Figure 5:
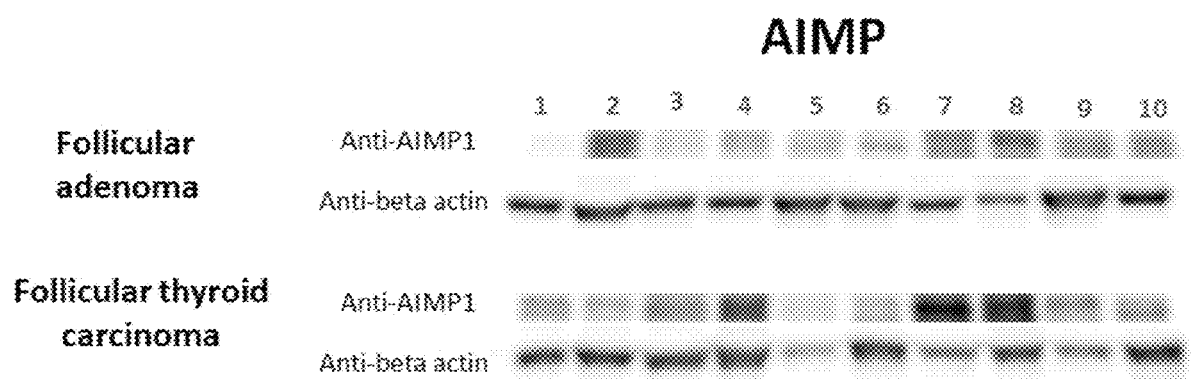
FIG. 5 shows Western blot results of AIMP1 protein levels in follicular adenoma and follicular thyroid carcinoma tissues, respectively.
Figure 6:
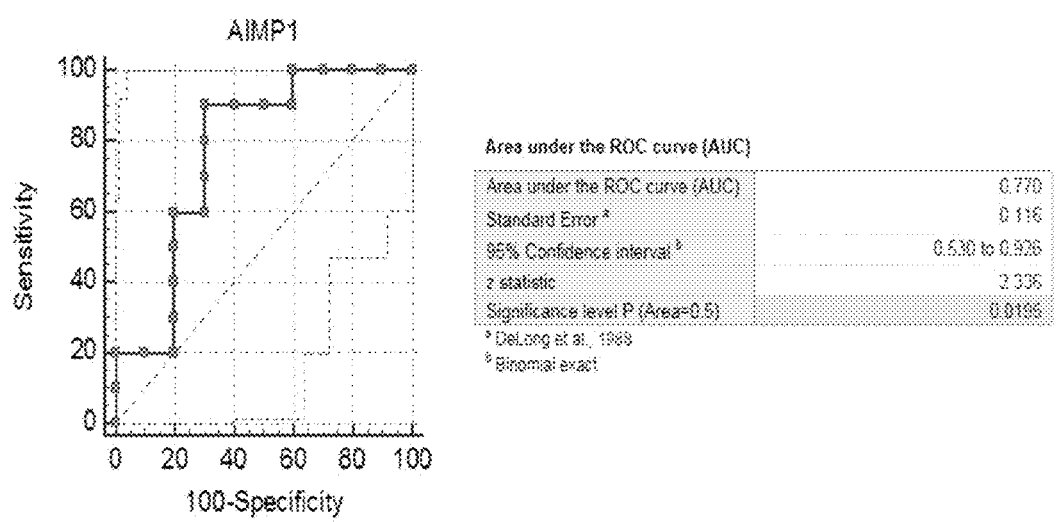
FIG. 6 show the result of Area Under Curve (AUC) calculation and Receiver Operating Characteristic (ROC) analysis via deriving the band intensity via western blot after confirming AIMP1 protein level in follicular adenoma and follicular thyroid carcinoma tissue by western blotting.
Figure 7:
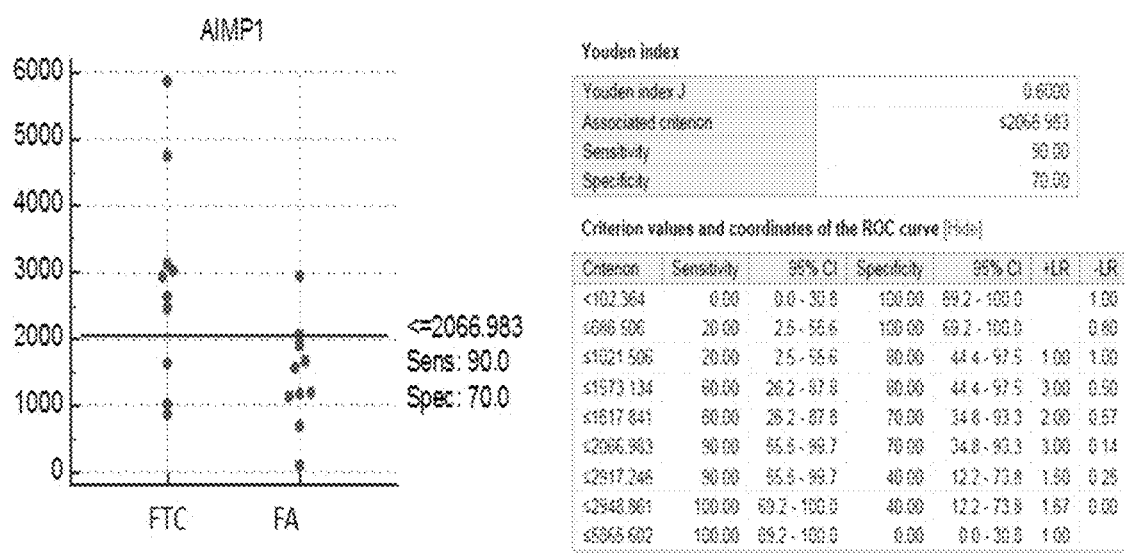
FIG. 7 shows the results of an Interactive plotting analysis for classification of follicular adenoma and follicular thyroid carcinoma by the measurement of AIMP1 protein level, confirming that AIMP1 was able to distinguish between follicular thyroid carcinoma and follicular adenoma with sensitivity of 90%, and specificity of 70%.

Among the FTC and FA-differentiating biomarkers in Example 3, AIMP1 was used as a representative, to confirm its detection ability described. The amount of AIMP1 protein in 10 follicular adenoma tissues and 10 follicular thyroid carcinoma tissues was analyzed by Western blot, respectively. Representative analysis results are shown in FIG. 5. Receiver Operating Characteristic (ROC) analysis was performed by deriving the band intensities and Area Under Curve (AUC) was calculated. As a result, the AUC was 0.770 and the significance level was 0.0195 (see FIG. 6). As shown in FIG. 7, the result of the interactive plotting analysis showed that the AIMP1 can distinguish the follicular thyroid carcinoma from follicular adenoma with the sensitivity of 90% and the specificity of 70%.

INDUSTRIAL APPLICABILITY

As described above, the ARS or AIMP protein types disclosed in the present invention are diagnostic markers that can differentially detect benign tumors such as follicular adenomas without tissue collection through surgery for follicular thyroid carcinoma in which a simple and definite diagnosis method is not available, thus being able to be used in fields such as an in vitro diagnostic industry.

What is claimed is:

1. A method for treating a follicular thyroid carcinoma, the method comprising the steps of:
   (a) obtaining a thyroid tissue sample from a human subject suspected of having follicular thyroid carcinoma;
   (b) measuring the protein expression level of an aminoacyl-tRNA synthetase (ARS) or an aminoacyl-tRNA synthetase complex-interacting multifunctional protein (AIMP) in the sample;
   (c) comparing the measured protein expression level of the subject with that of a control;
   (d) diagnosing the subject with a follicular thyroid carcinoma when the protein expression level of the subject has a change in comparison with that of the control; and
   (e) treating the diagnosed subject by conducting at least one of a chemotherapy, a surgery; and a radiation therapy.

2. The method of claim 1, herein the control is a patient identified as having thyroid follicular adenoma.

3. The method of claim 1, wherein the change in the protein expression level is an increase in the expression level of at least one protein selected from the group consisting of Aminoacyl tRNA synthase complex-interacting multifunctional protein 1 (AIMP1), Isoleucyl-tRNA synthetase mitochondrial (IARS mitochondrial), seryl-tRNA synthetase mitochondrial (SARS mitochondria), lysyl-tRNA synthetase (KARS); valyl-tRNA synthetase (VARS), and phenylalanyl-tRNA synthetase alpha subunit (FARSA).

4. The method of claim 1, wherein the change in the protein expression level is a decrease in the protein expression level of at least one protein selected from the group consisting of alanyl-tRNA synthetase (AARS), aspartyl-tRNA synthetase (DARS), bifunctional glutamyl-prolyl-tRNA synthetase (EPRS), tryptophanyl-tRNA synthetase (WARS), glycyl-tRNA synthetase (GARS), isoleucyl-tRNA synthetase cytoplasmic (IARS cytoplasmic), tyrosyl-tRNA synthetase (YARS), asparagyl-tRNA synthetase (NARS), glutaminyl-tRNA synthetase (OARS), arginyl-tRNA synthetase (RARS), seryl-tRNA synthetase cytoplasmic (SARS cytoplasmic) and threonyl-tRNA synthetase (TARS).

5. The method of claim 1, wherein the measurement of the protein expression level is performed by a method selected from the group consisting of western blotting, dot blotting, enzyme-linked immunosorbant assay (ELISA), radio immune assay (RIA), radial immunodiffusion assay, Ouchterlony immunodiffusion, rocket immunoelectrophoresis, immunohistochemistry, immunoprecipitation, complement fixation assay, Flow Cytometry (FRCS), protein chip and mass spectrometry.

6. The method of claim 1, wherein the aminoacyl-tRNA synthetase (ARS) is at least one selected from the group consisting of Isoleucyl-tRNA synthetase mitochondrial (IARS mitochondrial, GenBank GI No. 94730583), seryl-tRNA synthetase mitochondria (SARS mitochondria, GenBank GI No. 23822219), lysyl-tRNA synthetase (KARS, GenBank GI No. 20178333), valyl-tRNA synthetase (VARS, GenBank GI No. 1194845281), phenylalanyl-tRNA synthetase alpha subunit (FARSA, GenBank GI No. 12643946), alanyl-tRNA synthetase (AARS, GenBank GI No. 115502460), aspartyl-tRNA synthetase (GARS, GenBank GI No. 20178330), bifunctional glutamyl-prolyl-tRNA synthetase (EPRS, GenBank GI No. 288558855), tryptophanyl-tRNA synthetase (WARS, GenBank GI No. 135191), glycyl-tRNA synthetase (GARS, GenBank GI No. 313104283), isoleucyl-tRNA synthetase cytoplasmic (IARS cytoplasmic, GenBank GI No. 239938717), tyrosyl-tRNA synthetase (YAKS, GenBank GI No. 13638438), asparagyl-tRNA synthetase (NARS, GenBank GI No. 3915059), glutaminyl-tRNA synthetase (OARS, GenBank GI No. 1351170), arginyl-tRNA synthetase (BARS, GenBank GI No. 20178331), seryl-tRNA synthetase cytoplasmic (SARS cytoplasmic, GenBank GI No. 19860217) and threonyl-tRNA synthetase (TARS, GenBank GI No. 60267755).

7. The method of claim 1, wherein the aminoacyl-tRNA synthetase complex-interacting multifunctional protein (AIMP) is an aminoacyl-tRNA synthetase complex-interacting multifunctional protein 1 (AIMP1, GenBank GI No. 215490009).

8. The method of claim 1, wherein the step of measuring is conducted with a composition comprising an agent for measuring the expression level of an aminoacyl-tRNA synthetase (ARS) or an aminoacyl-tRNA synthetase complex-interacting multifunctional protein (AIMP).

9. The method of claim 8, wherein the aminoacyl-tRNA synthetase (ARS) is at least one selected from the group consisting of Isoleucyl-tRNA synthetase mitochondrial (IARS mitochondrial), seryl-tRNA synthetase mitochondria (SARS mitochondria), lysyl-tRNA synthetase (KARS), valyl-tRNA synthetase (VARS), phenylalanyl-tRNA synthetase alpha subunit (FARSA), alanyl-tRNA synthetase (AARS), aspartyl-tRNA synthetase (DARS), bifunctional glutamyl-prolyl-tRNA synthetase (EPRS), tryptophanyl-tRNA synthetase (WARS), glycyl-tRNA synthetase (GARS), isoleucyl-tRNA synthetase cytoplasmic (IARS cytoplasmic), tyrosyl-tRNA synthetase (YARS), asparagyl-tRNA synthetase (MARS), glutaminyl-tRNA synthetase (OARS), arginyl-tRNA synthetase (BARS), seryl-tRNA synthetase cytoplasmic (SARS cytoplasmic) and threonyl-tRNA synthetase (TARS).

10. The method of claim 8, wherein the aminoacyl-tRNA synthetase complex-interacting multifunctional protein (AIMP) is an aminoacyl-tRNA synthetase complex-interacting multifunctional protein 1 (AIMP1).

11. The method of claim 1, wherein the follicular thyroid carcinoma is differentially diagnosed from a follicular adenoma.

12. The method of claim 8, wherein the agent is a peptide, antibody, or aptamer comprising a binding domain specific for the ARS or AIMP protein.

13. The method of claim 8, wherein the composition comprising the agent is contained in a kit for diagnosing a follicular thyroid carcinoma.

* * * * *